US012767919B2

(12) United States Patent
Ott et al.

(10) Patent No.: US 12,767,919 B2
(45) Date of Patent: Oct. 20, 2026

(54) BIOCOMPATIBLE COMPOSITE ELEMENTS AND METHODS FOR PRODUCING

(71) Applicant: SCHOTT AG, Mainz (DE)

(72) Inventors: Christian Ott, Ampfing (DE); Robert Hettler, Kumhausen (DE); Christoph Stangl, Buch am Erlbach (DE); Helena Blümel, Frontenhausen (DE); Reinhard Ecker, Landshut (DE)

(73) Assignee: SCHOTT AG, Mainz (DE)

( * ) Notice: Subject to any disclaimer, the term of this patent is extended or adjusted under 35 U.S.C. 154(b) by 1463 days.

(21) Appl. No.: 16/893,510

(22) Filed: Jun. 5, 2020

(65) Prior Publication Data

US 2020/0399575 A1 Dec. 24, 2020

(30) Foreign Application Priority Data

Jun. 5, 2019 (DE) ..................... 10 2019 115 147.3

(51) Int. Cl.

*C12M 1/12* (2006.01)
*B29C 71/02* (2006.01)
*B32B 1/08* (2006.01)
*B32B 27/28* (2006.01)
*B32B 27/32* (2006.01)

(Continued)

(52) U.S. Cl.

CPC ............... *C12M 37/04* (2013.01); *B32B 1/08* (2013.01); *B32B 27/288* (2013.01); *B32B 27/32* (2013.01); *C08J 7/08* (2013.01); *C12M 23/02* (2013.01); *C12M 23/06* (2013.01); *C12M 23/22* (2013.01); *C12M 23/46* (2013.01); *C12M 31/02* (2013.01);

(Continued)

(58) Field of Classification Search

CPC ...................................................... C12M 23/22

See application file for complete search history.

(56) References Cited

U.S. PATENT DOCUMENTS 1,808,760 A 6/1931 Bills
3,803,700 A 4/1974 Tischlinger (Continued)

FOREIGN PATENT DOCUMENTS

CN 1922484 2/2007
CN 201064439 5/2008

(Continued)

OTHER PUBLICATIONS

Damdar et al. (Proceedings of the ASME Symposium on Elevated Temperature Application of Materials for Fossil, Nuclear, and Petrochemical Industries Mar. 25-27, 2014) (Year: 2014).*

(Continued)

*Primary Examiner* — Liam J Heincer

(74) *Attorney, Agent, or Firm* — Ruggiero McAllister & McMahon LLC

(57) ABSTRACT

A biocompatible composite element for a bioreactor is provided that includes an outer frame and an inner component. The outer frame is a polymeric material. The outer frame can be inseparably attached to a wall of the bioreactor. The inner component is a transparent material selected from a group consisting of glass, sapphire, and glass ceramic. The inner component is secured in the outer component in an inseparable hermetically tight manner. The inner component is configured for a spectral process control through the transparent material of the inner component.

19 Claims, 10 Drawing Sheets

(51) Int. Cl.
*C12M 1/00* (2006.01)
*C12M 3/00* (2006.01)

(52) U.S. Cl.
CPC ..... *B32B 2307/412* (2013.01); *C08J 2323/06* (2013.01); *C08J 2371/10* (2013.01)

(56) References Cited

U.S. PATENT DOCUMENTS

| | | | | |
|---|---|---|---|---|
| 4,573,761 | A | 3/1986 | McLachlan | |
| 4,577,110 | A | 3/1986 | MacBride | |
| 4,768,879 | A | 9/1988 | McLachlan | |
| 4,803,365 | A * | 2/1989 | Krause | C12M 41/36 250/461.1 |
| 4,893,935 | A | 1/1990 | Mandel | |
| 4,909,588 | A | 3/1990 | Harner | |
| 5,237,984 | A | 8/1993 | Williams, III | |
| 5,413,092 | A | 5/1995 | Williams, III | |
| 5,530,065 | A | 6/1996 | Farley | |
| 5,709,724 | A | 1/1998 | Naugler | |
| 5,774,610 | A | 6/1998 | O'Rourke | |
| 5,944,324 | A | 8/1999 | Schultheis | |
| 6,478,730 | B1 | 11/2002 | Bala | |
| 6,531,341 | B1 | 3/2003 | Peterson | |
| 6,831,739 | B2 | 12/2004 | Slater | |
| 7,184,142 | B2 | 2/2007 | Komachi | |
| 8,565,848 | B2 * | 10/2013 | Brister | A61B 5/14532 600/347 |
| 8,974,656 | B2 | 3/2015 | Trimmer | |
| 9,250,126 | B2 | 2/2016 | Barlow | |
| 2001/0048525 | A1 * | 12/2001 | Slater | G01N 21/8507 356/417 |
| 2002/0087047 | A1 | 7/2002 | Remijan | |
| 2003/0083552 | A1 | 5/2003 | Remijan | |
| 2003/0147132 | A1 | 8/2003 | Behnsen | |
| 2004/0055402 | A1 | 3/2004 | Pensis | |
| 2006/0240546 | A1 * | 10/2006 | Goodwin | C12M 23/14 435/289.1 |
| 2007/0041869 | A1 | 2/2007 | Zimmer | |
| 2007/0292940 | A1 | 12/2007 | Roell | |
| 2008/0032064 | A1 | 2/2008 | Gordon | |
| 2008/0032389 | A1 | 2/2008 | Selker | |
| 2008/0171383 | A1 * | 7/2008 | Selker | C12M 41/32 435/288.7 |
| 2009/0311776 | A1 | 12/2009 | Kelly | |
| 2010/0035337 | A1 * | 2/2010 | Bahnemann | C12M 27/02 435/292.1 |
| 2010/0129899 | A1 | 5/2010 | Oosterhuis | |
| 2010/0255458 | A1 | 10/2010 | Kinkaid | |
| 2010/0304065 | A1 | 12/2010 | Tomantschger | |
| 2011/0124035 | A1 * | 5/2011 | Broadley | C12M 23/28 435/29 |
| 2011/0170177 | A1 * | 7/2011 | Meissner | G02B 7/02 359/830 |
| 2012/0244608 | A1 * | 9/2012 | Selker | C12M 23/28 435/283.1 |
| 2012/0291238 | A1 | 11/2012 | Barnfield Frej | |
| 2013/0039810 | A1 * | 2/2013 | Riechers | C12M 41/02 422/82.05 |
| 2013/0102846 | A1 * | 4/2013 | Sjostrom | A61B 1/07 600/110 |
| 2013/0145818 | A1 | 6/2013 | Allgaeuer | |
| 2014/0024112 | A1 | 1/2014 | Galiano | |
| 2014/0054186 | A1 * | 2/2014 | Riechers | C12M 41/00 356/246 |
| 2014/0071453 | A1 * | 3/2014 | Riechers | G01N 21/8507 356/436 |
| 2014/0349385 | A1 * | 11/2014 | Erdenberger | B01F 35/4122 435/302.1 |
| 2015/0108721 | A1 | 4/2015 | Thuillier | |
| 2015/0345689 | A1 * | 12/2015 | Selker | B65B 55/16 422/534 |
| 2016/0109538 | A1 | 4/2016 | Fujii | |
| 2016/0136929 | A1 | 5/2016 | Meiss | |
| 2016/0216154 | A1 | 7/2016 | Hofmeister | |
| 2017/0108427 | A1 | 4/2017 | Machuca | |
| 2017/0184499 | A1 | 6/2017 | Hoehne | |
| 2019/0309241 | A1 * | 10/2019 | Ott | C12N 1/12 |
| 2019/0309253 | A1 * | 10/2019 | Ott | C12M 37/04 |
| 2019/0309255 | A1 * | 10/2019 | Ott | C12M 37/04 |
| 2020/0208094 | A1 * | 7/2020 | Höhse | G01N 21/01 |
| 2020/0345211 | A1 * | 11/2020 | Austin | A61B 1/00068 |
| 2020/0381147 | A1 * | 12/2020 | Hettler | H01B 1/02 |
| 2020/0399575 | A1 | 12/2020 | Ott | |
| 2021/0040429 | A1 * | 2/2021 | Ott | C12M 41/00 |
| 2021/0130758 | A1 * | 5/2021 | Ott | C12M 41/46 |
| 2021/0251509 | A1 * | 8/2021 | Hettler | G02B 6/4203 |
| 2021/0283860 | A1 | 9/2021 | Van Der Straeten | |
| 2022/0135398 | A1 * | 5/2022 | Thomas | B81C 1/00269 257/415 |
| 2022/0157684 | A1 * | 5/2022 | Zetterer | B23K 26/28 |
| 2022/0219972 | A1 * | 7/2022 | Hettler | B81C 1/00317 |
| 2022/0348457 | A1 * | 11/2022 | Zetterer | B81C 1/00904 |

FOREIGN PATENT DOCUMENTS

| | | |
|---|---|---|
| CN | 101264003 | 9/2008 |
| CN | 101724548 | 6/2010 |
| CN | 102228377 | 11/2011 |
| CN | 102706810 | 10/2012 |
| CN | 107868756 | 4/2018 |
| CN | 109620315 | 4/2019 |
| DE | 4414975 | 11/1995 |
| DE | 19615371 | 10/1997 |
| DE | 19745663 | 5/1999 |
| DE | 10016838 | 10/2001 |
| DE | 102005035914 | 2/2007 |
| DE | 102008036934 | 2/2010 |
| DE | 102008048333 | 4/2010 |
| DE | 102010007559 | 8/2011 |
| DE | 102011101107 | 11/2012 |
| DE | 102011101108 | 11/2012 |
| DE | 102013007205 | 3/2014 |
| DE | 102013214422 | 1/2015 |
| DE | 102015226022 | 6/2016 |
| DE | 202016000554 | 5/2017 |
| DE | 102016008826 | 1/2018 |
| DE | 102016215493 | 2/2018 |
| DE | 102016215500 | 2/2018 |
| DE | 102017010629 | 5/2019 |
| DE | 102018108323 | 10/2019 |
| DE | 102018108327 | 10/2019 |
| DE | 102019115147 | 1/2021 |
| EP | 2573548 | 3/2013 |
| EP | 3553160 | 10/2019 |
| GB | 495798 | 11/1938 |
| GB | 2236253 | 4/1991 |
| WO | 8704247 | 7/1987 |
| WO | 2005068059 | 7/2005 |
| WO | 2005108549 | 11/2005 |
| WO | 2006017951 | 2/2006 |
| WO | 2009017721 | 2/2009 |
| WO | 2015142805 | 9/2015 |
| WO | 2018129122 | 7/2018 |

OTHER PUBLICATIONS

Shen et al. (Nuclear Engineering and Technology 48, 2016, 533-544) (Year: 2016).*

Zitzenbacher, "Calculation of the Contact Angle of Polymer Melts on Tool Surfaces from Viscosity Parameters", MDPI, Polymers, Dec. 30, 2017, 12 pages.

Wikipedia, "Optical contact bonding" Oct. 14, 2021, https://en.wikipedia.org/w/index.php?title=Optical_contact_bonding&oldid=859369785, 4 pages.

Bluma, "In-situ imaging sensors for bioprocess monitoring: of the art", Springer, Anal Bioanal Chem, Aug. 30, 2010, 10 pages.

Chanda, "Industrial Polymers, Specialty Polymers, and Their Applications", CRC Press, Plastics Engineering Series, 2009, 8 pages.

"Guidance for Industry Sterile Drug Products Produced by Aseptic Processing—Current Good Manufacturing Practice" U.S. Depart-

(56) References Cited

OTHER PUBLICATIONS ment of Health and Human Services Food and Drug Administration Center for Drug Evaluation and Research (CDER) Center for Biologics Evaluation and Research (CBER) Office of Regulatory Affairs (ORA), Sep. 2004, 64 pages.
Chisti, "Build Better Industrial Bioreactors", Chemical Engineering Progress, Materials, Jan. 1992, 4 pages.
Gruber, "Lab on a Chip—Integration and Application of Optical Chemical Sensors in Microbioreactors", 2017, 46 pages.
A42 IMTEC@, "Strengthen plastic components. Ill heavy-duty threaded inserts. A strong connection", Bollhoff, 2017, 4 Pages.
A30 Rudolph, "Development and use of inline microscopic methods for the observation of biotechnological processes", dissertation, Hanover, 2007, 144 Pages.
A32 Quitter, "Fabric and form-fitting connection of plastic and glass", Plastic Glass Joint, Jan. 27, 2012, construction praxl, 2 pages.
A33 KM Plastic Magazine, "Safe encapsulation of tempered glass", Overmold Glass, 2011, 2 pages.
A34 Satzge, "Integrated All Around", Plastverasbeiter, Jun. 2007, 3 pages.
A35, "Investments against the trend", Suppliers: Success with metal and plastics expertise, Mar. 16, 2009, 4 pages.
A36 Wikipedia, "Aufschrumpfen", (Shrink-fitting) Jan. 14, 2019, with English translation, 4 pages.
A39 Domininghaus, "Plastics—Properties and applications", Springer, 2008, 13 pages.
Din En 1779, "Non-destructive testing—Leak testing Criteria for method and technique selection", Oct. 1999, 20 Pages.
ISO 10993-1, "Biological evaluation of medical devices—Part 1: Evaluation and testing within a risk management process", Fifth Edition, Aug. 2018, 48 pages.
ASTM D543-06, "Standard Practices for Evaluating the Resistance of Plastics to Chemical Reagents1", Jun. 2006, 7 pages.
Holtkamp, "Advances in hybrid laser joining", The International Journal of Advanced Manufacturing Technology, vol. 47, Jun. 13, 2009, pp. 923-930.
Timesavers, "Everything you need to know about surface roughness (RA)", Jul. 29, 2021, https://www.timesaversint.com/de/Wissensdatenbank/alles-was-sie-ue . . . , 12 pages, with English translation.
Baburaj, "Enhancement of adhesive joint strength by lasersurface modification", ScienceDirect, International Journal of Adhesion and Adhesives, vol. 27, Issue 4, Jun. 2007, 5 pages.
Byskov-Neilsen, "Ultra-high-strength micro-mechanical interlocking by injection molding into laser-structured surfaces", ScienceDirect, International Journal of Adhesion and Adhesives, vol. 30, Issue 6, Sep. 2010, 4 pages.

* cited by examiner

FIG. 16
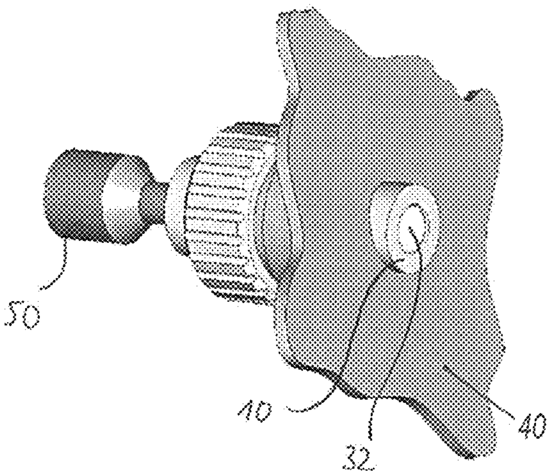
FIG. 17
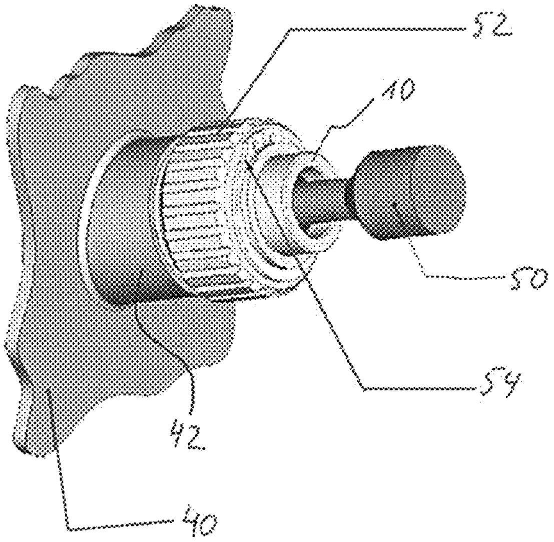
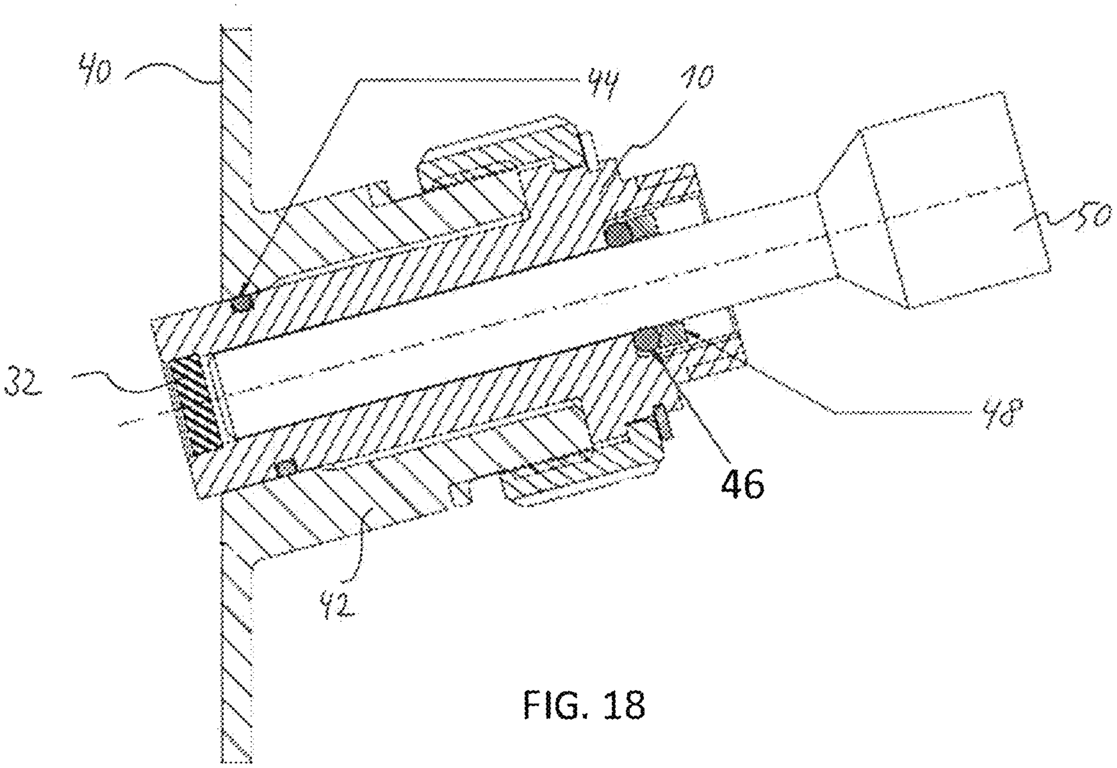
FIG. 18

BIOCOMPATIBLE COMPOSITE ELEMENTS AND METHODS FOR PRODUCING

CROSS REFERENCE TO RELATED APPLICATIONS

This application claims benefit under 35 USC § 119 of German Application 10 2019 115 147.3 filed Jun. 5, 2019, the entire contents of which are incorporated herein by reference.

BACKGROUND

1. Field of the Invention

The invention relates to the spectral process control of production processes in bioreactors.

2. Description of Related Art

Bioreactors serve for the culturing of microorganisms and of animal and plant cells and thereby open up a broad field for the application of biotech production processes. In general, there exists a need for further optimization of these processes. For the production of biopharmaceuticals, in particular, there is a push for improvements in product yield and thus increases in profit. Various approaches are available for increasing product yield, for minimizing contamination risks, and for reducing costs.

On the one hand, the control of the processes and thus the yield can be optimized by carrying out a real-time process control of key parameters. In particular, spectroscopic methods in which a measurement is possible from outside of the bioreactor are suitable for this purpose, because, in this way, risks of contamination are prevented.

In the case of a bioreactor having a stainless steel culture vessel, such measurements are made possible, for example, by mounting a flanged connector fitting that has a viewing port in order to create a window into the interior of the bioreactor. Such connector fittings can be designed, for example, as a metal-glass composite and can form, for example, a so-called glass-to-metal seal (GTMS).

On the other hand, cost savings in biotech production processes can also be achieved by replacing traditional stainless steel bioreactors by single-use bioreactors (also referred to as disposable reactors). The single-use materials employed in this case, in particular presterilized plastics, make possible marked reductions in costs, depending on the intended application, not only in the procurement of these materials, but also in operation, in particular through the avoidance of repeated cleaning and sterilization and the cleaning validation associated therewith.

In the case of single-use reactors, the yield also depends crucially on determining substrate and product concentrations. Nonetheless, for single-use applications, an in situ process control in accordance with the prior art is not yet adequately available. The use of glass-to-metal seals (GTMS) is not adequately offered in the case of single-use applications.

It is therefore customary in the industry sector to take samples during culturing. The time involved for this is considerable. This owes to the sampling itself, with which a risk of contamination is associated, as well as to resource-intensive offline analysis. In spite of these efforts, the process control, in particular for single-use applications, is impaired by the lack of real-time data.

SUMMARY

The object of the invention is accordingly based on being able to provide a spectral process control and/or real-time data in the case of single-use bioreactors as well. An aspect of the object is accordingly to provide an alternative to the use of glass-metal connector fittings, in particular for applications in which glass-to-metal seals (GTMS) are not preferred.

In accordance with the invention, a biocompatible composite element, in particular for use as a connector fitting for bioreactors or other tanks, preferably as a connector fitting for single-use bioreactors, is provided.

The composite element comprises an outer frame that is made with or from a polymeric material, in particular for attachment to a wall of a bioreactor, preferably for inseparable attachment to a wall of a single-use bioreactor, and an inner component that is made with or from a transparent material, such as, for example, glass, in particular borosilicate glass, quartz, sapphire, or glass ceramic. The inner component is fitted in the outer frame in a sterilely tight manner, preferably in a hermetically tight manner, and forms a window, in particular in order to enable a spectral process control from outside of a bioreactor. In this case, the inner component is fitted in the outer frame, in particular in an inseparable manner, that is, in a permanently fixed manner.

The composite element particularly forms an at least sterilely tight and preferably hermetic seal between the polymer frame and the inner component. In particular, when the inner component is composed of glass or comprises glass, the term glass-to-polymer seal (GTPS) is applicable. What are involved therefore, are particularly seals in material combination with polymers. Coming into consideration as polymers for the outer frame, in particular in the form of homo-, co-, or terpolymers, are, in particular, polyethylene (PE), polypropylene (PP), polyamide (PA), polyethylene terephthalate (PET), ethylene vinyl alcohol (EVOH), polyether ether ketone (PEEK), polyaryl ether ketone (PAEK), polysulfone (PSU), and polyphenylene sulfide (PPS).

Sterilely tight is understood in the sense of the present invention to mean a seal that exhibits a minimum sealing effect. The sealing effect is determined by way of a leakage rate test using helium in accordance with the vacuum method A3 of DIN EN 1779. In this method, a composite element according to the invention is subjected to a time-dependent test. The term sterilely tight applies when the rate of helium leakage after 2 minutes has a value of less than $6 \cdot 10^{-4}$ mbar·L/s. A preferred form of the sterile sealtightness exists when the rate of helium leakage over a time period of 2 minutes has a value of less than $10^{-8}$ mbar·L/s. Advantageously, these rates of leakage are each reached also in the case of a test over 4 minutes.

Even more preferred is a hermetic seal. A seal is referred to as hermetically tight when it exhibits a rate of helium leakage of less than $1.69 \cdot 10^{-10}$ mbar·L/s.

The composite element or the glass-to-polymer seal is designed, in particular, for a universal industrial usability. In particular, the composite element or glass-to-polymer seal is suitable for disposable/single-use bioreactors. In particular, in the case of single-use bioreactors, the polymer outer frame makes possible the sterilely tight welding to the outer wall of the bioreactor—for example, polyethylene (PE) to polyethylene (PE). Accordingly, the polymeric material of the outer frame can correspond to the polymer of the bioreactor. However, different materials are also possible. Accordingly, the composite element can be welded in a permanently fixed manner to a wall of a bioreactor, so that it can no longer be separated from the wall.

As described, the composite element according to the invention is biocompatible. Herewith associated is, in particular, the fact that, during culturing in bioreactors, no undesired microbes can adhere to the composite element and/or can grow on it. Particularly critical are the areas of connection between glass and polymer and/or metal and polymer. The biocompatibility, that is, in particular, the suppression of the detrimental adherence of microbes and/or of the detrimental growth of microbes can be achieved by having no edge angles of 90° or greater at the material transitions mentioned. Obviously, what is understood here is the edge angle on the microscopic scale that is decisive for microbes. Clearly, the composite element can have elements and/or areas that are arranged perpendicularly to the optical element. The invention provides rather that the microscopic edge angles between glass and polymer and/or metal and polymer are less than 90°. This is achieved, for example, in that, during production, the polymer covers the glass and/or metal with edge angles of less than 90° or in that, for example, directly after a material transition from metal to polymer or from glass to polymer, arched recesses are introduced in the polymeric material (for this, see also the figures and the description thereof). Advantageously, it is also possible to provide a wetting angle of contact or an edge angle between the materials of less than 85°.

It is accordingly preferably provided that, on a scale that is decisive for the growth of microbes, at least one, preferably the majority, and most preferably all edge angles between different materials are less than 90° and preferably less than 85°. In this way, zones that favor microbial sources and thus are detrimental to sterilizability are prevented at the transitions of different materials (for example, polymer-glass). The wetting angle is governed, in particular, by the polymer-specific adhesion between the macromolecules and the other material.

In accordance therewith, the principle of the invention provides that a composite element, which has an outer frame made from or with a polymeric material, can be provided and can be employed rationally, in particular, for single-use bioreactors and, on the other hand, is surprisingly capable of creating a sterilely tight and biocompatible connection, as a result of which the optical functionality for culturing in such bioreactors is provided.

The invention thus makes possible, in general, a higher product yield and a more efficient process development by way of an improved process control. In particular, the invention makes possible applications of spectral in-situ process control in a sterile and reliable manner.

Decisive for the development and control of biotech production processes are sterile conditions and real-time measurements of key parameters for the development and control of biotech production processes.

Presterilized single-use products are of special significance in this regard. Sterile culturing conditions are obligatory, for which reason no risk of contamination should ensue from a measurement. For single-use applications, the sterilizability requirement that is customary to the sector is, in particular, gamma radiation. In biotechnology and particularly for the production of biopharmaceuticals, only approved materials are permitted.

In order to meet the stringent requirements for the production of biopharmaceuticals, the materials of the composite element can be chosen in such a way that they each conform to the following standards: FDA approved materials (ICH Q7A, CFR 211.65(a)—Code of Federal Regulations, USP Class, animal derivative free, bisphenol A free); EMA (European Medicines Agency) EU GMP Guide Part II approved materials; Sectoral chemical resistance—ASTM D 543-06; Biocompatibility, e.g., referred to US Pharmacopeia or tests referred to ISO 10993

The polymer outer frame of the composite element according to the invention can be designed in different ways.

In particular, the outer frame of the composite element can be annular in design such that, in cross section, the outer frame completely surrounds the inner component. In this case, the cross section of the inner component can be of any shape, in particular round or circular.

Moreover, the outer frame can be tubular in design and hence have a first (for example, proximal) and a second (for example, distal) end of the tube, in particular such that the outer frame can be attached by the first end of the tube to the wall of the bioreactor.

Moreover, the outer frame preferably has a flange, in particular for attachment to the wall of a bioreactor, such as, for example, a single-use bioreactor. When the outer frame is tubular in design, the flange is preferably arranged between the first end and the second end of the tube, but also can be arranged at the first end of the tube. The flange can be joined in an inseparable manner to the wall of the bioreactor, preferably in a permanently fixed manner; for example, the flange can be welded to the wall.

The flange and the outer frame are preferably of one piece and monolithic in design and, in particular, are formed from or with the same polymeric material. The polymer flange can then be welded in a sterilely tight manner to the wall of a polymeric tank, in particular to the outer wall of a single-use bioreactor.

Furthermore, the outer frame preferably has a thread, which, in particular, is designed as an outer thread, with the thread preferably being arranged at the first end of the tube.

The inner component of the composite element can also be designed in different ways.

In one variant, the inner component is designed in one part, namely, in particular, as a plate- or disc-shaped, transparent structural part, whereby this transparent structural part is fitted in the outer frame in a sterilely tight manner and/or in a hermetically tight manner, preferably in a permanently fixed manner or in an inseparable manner. The transparent structural part can be, for example, a glass plate or disc. Here, the glass of the transparent structural part comprises, for example, quartz glass or borosilicate glass or is composed thereof. However, the transparent structural part can also be designed, for example, as a sapphire plate or disc.

Preferably, the transparent structural part exhibits a transmittance that is greater than 75%, in particular greater than 90%, in a spectral range with a wavelength of 190 to 5500 nm. More preferably, the transparent structural part exhibits a transmittance that is greater than 75%, preferably greater than 80%, even more preferably greater than 90%, in a spectral range with a wavelength of 190 to 2800 nm. Still more preferably, the transparent structural part exhibits a transmittance that is greater than 75%, most preferably greater than 90%, in a spectral range with a wavelength of 190 to 2700 nm.

Moreover, the transparent structural part is, in particular, of one piece and monolithic in design. When the outer frame is tubular in design, the transparent structural part is preferably arranged at the second end of the tube or extends essentially to the second end of the tube, whereby it is possible to provide for a tubular overhang.

In another variant, the inner component of the composite element is at least two-part in design, namely, with a transparent structural part that is, in particular, disc-shaped and, in addition, a connecting part that is, in particular, annular or tubular in shape.

In this case, the connecting part is joined both to the transparent structural part and to the outer frame. The connection between the connecting part and the transparent structural part is formed in a sterilely tight manner, preferably in a hermetically tight manner, and can also be formed in a permanently fixed manner or in an inseparable manner. Likewise, the connection between the connecting part and the outer frame is also formed in a sterilely tight manner, preferably in a hermetically tight manner and preferably in a permanently fixed manner or in an inseparable manner.

As described above, the transparent structural part can be, in turn, particularly of one piece and monolithic in design. Furthermore, the connecting part is also preferably of one piece and monolithic in design. The transparent structural part is preferably arranged at the second end of the tube and the connecting part preferably extends up to the first end of the tube.

Preferably, in cross section, the connecting part completely surrounds the transparent structural part in such a way that the transparent structural part is fitted in the connecting part in a sterile manner and/or in a hermetically tight manner, preferably in a permanently fixed manner or in an inseparable manner, and the connecting part is fitted in the outer frame, in turn, in a sterile manner and/or in a hermetically tight manner, preferably in a permanently fixed manner or in an inseparable manner.

It can further be provided that the transparent structural part is in contact exclusively with the connecting part. The transparent structural part is then joined only indirectly to the outer frame.

The connecting part is preferably made with or from metal, in particular a stainless steel, such as, for example, an austenitic-ferritic duplex steel.

It can also be provided that, first of all, in cross section, the connecting part encloses a frame, which, for example, is made with or from glass and surrounds the transparent structural part, in such a way that the transparent structural part is fitted in the frame in a sterilely tight manner and preferably in a hermetically tight manner, and the connecting part, in turn, is fitted in the outer frame in a sterilely tight manner and preferably in a hermetically tight manner.

The connecting part preferably has a profile for increasing the contact area with the outer frame. For example, it is possible to provide grooves in the outer surface of the connecting part. In regard to the material composite strength and/or angle of contact, it is also possible, in particular, to provide a microstructure, which, for example, can be produced by laser processing. Thus, the surface of the connecting part can have a first bunch of grooves that is formed by a plurality of grooves that extend parallel to one another and is crossed by a second bunch of grooves, so that a plurality or large number of projections are created between the grooves (for this, see also FIGS. 14 and 15).

Moreover, alternatively or cumulatively, it can be provided that, at its front end, the connecting part adjoins the transparent structural part and/or, at its front end, is joined to the transparent structural part in such a way that both the transparent structural part and the connecting part are each fitted in the outer frame in a sterile manner and/or in a hermetically tight manner, whereby, in each case, this fit occurs preferably in a permanently fixed manner or in an inseparable manner.

In particular, in the case of a front-end connection, but also otherwise, the connecting part can be made with or from a transparent material, in particular the same material as the transparent structural part, such as, for example, glass, sapphire, ceramic, or glass ceramic. In other words, the composite element can be designed, for example, as a glass/glass/polymer composite, as a sapphire/glass/polymer composite, as a sapphire/sapphire/polymer composite, as a glass/ceramic/polymer composite, as a sapphire/ceramic/polymer composite, as a ceramic/ceramic/polymer composite, etc. As explained in detail further below, the surface areas that adjoin each other can be designed as coherent areas.

On the other hand, however, the connecting part can also be made with or from a non-transparent material, preferably ceramic or metal, in particular an oxidizable metal, such as, for example, aluminum, whereby, most preferably, the connecting part has an oxide layer on a surface that adjoins the transparent structural part. The oxide layer can have a thickness of at least 5 micrometers, preferably at least 10 micrometers. In other words, the connecting part can be designed in the form of its oxide at the joining surface. By fabricating the connecting part with or from an oxidizable metal, it is possible for the joining area to be adjusted to the melting point of the transparent structural part, so that laser welding comes into consideration. If the connecting part is fabricated from aluminum (melting point 660° C.), for example, and forms an oxide layer of up to 30 μm, for example, at the joining area, the melting point in this $Al_2O_3$ zone is increased to 2050° C. The joining area can thus be adjusted to the melting point of a transparent structural part that is made of sapphire, for example, and hence can undergo laser welding. Reference is made to the GESTIS material database for the given temperature values.

The composite element, in particular in the case of a one-part design, but also in general, can accommodate compressive stresses. In particular, the inner component can be fitted under compressive stress so as to be fitted vertically in the outer frame.

This can be achieved, in particular, in that the composite element is produced or can be produced as follows: The outer frame is caused to expand with respect to the inner component (or, vice versa, the inner component is caused to contract); afterwards, the inner component, in particular the transparent structural part, is inserted in the outer frame and then the outer frame is caused to contract with respect to the inner component (or, vice versa, the inner component is caused to expand).

In particular, in this embodiment, but also independently thereof, the outer frame can be formed with or be made from polyether ether ketone (PEEK).

A composite element that accommodates compressive stresses can be produced, for example, by providing, first of all, an outer frame and an inner component, whereby the inner component is oversized with respect to the outer frame. The outer component (or the outer frame and the inner component) can then be heated, for example, to a temperature of at least 100° C., preferably at least 150° C. (for example, 200° C.), so that the outer frame expands (or expands more strongly than the inner component) and the oversize of the inner component vanishes or preferably decreases. The inner component can accordingly also continue to exhibit an oversize when the inner component is inserted in the outer frame. For example, it is possible here to provide an oversize of more than 0.01 mm, preferably of more than 0.03 mm (for example, 0.04 mm). On the other hand, too large an oversize may be no longer practicable, so that the oversize is preferably less than 0.2 mm and still more preferably less than 0.1 mm. It can accordingly be provided that the inner component is inserted in the outer frame already by producing compressive stress. In this case, it is possible to provide for producing compressive stress of more than 10 MPa, preferably more than 20 MPa, especially preferably more than 30 MPa. When, afterwards, the outer component is cooled (for example, to 22° C.), the compressive stress can further increase. For example, it can be provided that a compressive stress of more than 50 MPa, preferably more than 75 MPa, or most preferably more than 100 MPa is built up.

Regardless of whether the inner component is inserted in the outer frame with or without an oversize, it is advantageous when, ultimately, angled at an end of the tube of a tubular outer frame, the compressive stress decreases, as a rule, toward the outer end (critical end). Preferably, however, it is provided that the smallest compressive stress (at the critical end) that arises is still more than 1 MPa, preferably more than 5 MPa, or most preferably more than 10 MPa (for example, 11 MPa).

It can also be provided, particularly in the case of a two-part design, but also in general, that the inner component is fitted in the outer frame in a stress-neutral manner.

This can be achieved, for example, by producing or being able to produce the composite element as follows: The outer frame is affixed from the outside to the inner component, in particular to the connecting part and/or to the transparent structural part—for example, in that liquid polymeric material is fed from the outside onto the inner component and afterwards hardened.

In particular in this embodiment, but also independent thereof, the outer frame can be formed with or be made from polyethylene (PE).

When the transparent structural part is fitted in the connecting part, it can optionally be provided that the transparent structural part is under compressive stress. This comes into consideration, in particular, for the case of a metallic connecting part, but also in general.

A transparent structural part that is fitted under compressive stress in the connecting part can be achieved, in particular, by producing or being able to produce the inner component as follows: The connecting part is caused to expand with respect to the transparent structural part (or vice versa); afterwards, the transparent structural part is inserted in the connecting part and then the connecting part is caused to contract once again with respect to the transparent structural part (or vice versa).

When, at its front end, the transparent structural part is joined to the connecting part, but also in general, it can be provided that the transparent structural part is joined to the connecting part in a stress-neutral manner. This comes into consideration, in particular, for the case of a connecting part that is fabricated from or with the same material as the transparent structural part, but also in general.

A stress-neutral connection can be achieved, in particular, by producing or being able to produce the inner component as follows: The connecting part is pushed, at its front end, onto the transparent structural part and, afterwards, the connecting part is joined to the transparent structural part, preferably in a fixed manner and in particular by laser welding.

The process sequences described above are described once again in detail below:

A biocompatible composite element can accordingly be produced, for example, in accordance with the following process steps, in particular in this sequence:

Providing an outer frame that is made with or from a polymeric material, in particular polyether ether ketone (PEEK), and providing an inner component that is made with or from a transparent structural part, in particular made with or from glass, sapphire, or glass ceramic.

Causing a relative expansion of the outer frame with respect to the inner component, in particular by heating the outer frame or preferably by joint heating of the outer frame and the inner component.

Inserting the inner component, in particular the transparent structural part, in the outer frame that has been expanded with respect to the inner component.

Causing a relative contraction of the outer frame with respect to the inner component, in particular by cooling the outer frame or preferably by joint cooling of the outer frame and the inner component, so that the outer frame fits the inner component in a hermetically tight manner.

In other words, in step b) and correspondingly in step d), the outer frame (or the outer frame and the inner component) can be subjected to a positive or negative thermal expansion in such a way that, between the outer frame and the inner component, a temperature-dependent thermal expansion differential is achieved, whereby, in particular, in step b), a positive thermal expansion (expansion) and, in step d), a negative thermal expansion (contraction) is conducted.

A biocompatible composite element can further be produced, for example, in accordance with the following process steps, in particular in this sequence:

Providing an inner component and liquid polymeric material for the formation of an outer frame.

Feeding the liquid polymeric material from the outside onto the inner component, in particular onto the connecting part and/or onto the transparent structural part.

Hardening the liquid polymeric material in such a way that an outer frame that fits the inner component in a sterilely tight manner, preferably in a hermetically tight manner, is formed.

In the steps a), in order to provide the inner component, the above-described process sequences can precede the following process steps, in particular in this sequence:

Providing a transparent structural part and a connecting part, in particular made of metal.

Causing a relative expansion of the connecting part with respect to the transparent structural part, in particular by heating the connecting part or preferably by joint heating of the connecting part and the transparent structural part.

Inserting the transparent structural part in the connecting part that has been expanded with respect to the transparent structural part.

Causing a relative contraction of the connecting part with respect to the transparent structural part, in particular by cooling the connecting part or preferably by joint cooling of the connecting part and the transparent structural part, so that the connecting part is joined to the transparent structural part for the inner component, in particular in a sterilely tight manner and/or in a hermetically tight manner.

In other words, in step bb) and correspondingly in step dd), the connecting part (or the connecting part and the transparent connecting part) can be subjected to a positive or negative thermal expansion in such a way that, between the connecting part and the transparent structural part, a temperature-dependent thermal expansion differential is achieved, whereby, in particular, in step bb), a positive thermal expansion (expansion) and, in step dd), a negative thermal expansion (contraction) is conducted.

In the steps a), in order to provide the inner component, it is also possible, on the other hand, for the following process steps, in particular in this sequence, to be carried out beforehand:

Providing a transparent structural part and a connecting part, in particular made of the same material as the transparent structural part.

Guiding or pushing the connecting part, at its front end, to or onto the transparent structural part, so that the connecting part along with the transparent structural part is joined to the inner component, in particular in a sterilely tight manner and/or in a hermetically tight manner.

Preferably, laser welding the two connecting parts, so that the connecting part is joined to the transparent structural part for the inner component, in particular in a sterilely tight manner and/or in a hermetically tight manner and in a permanent manner.

All process sequences for producing a biocompatible composite element further comprise preferably, in particular as a concluding step, sterilizing, in particular autoclaving, the composite element that comprises the outer frame and the inner component fitted in it in a sterilely tight manner and/or in a hermetically tight manner.

Moreover, the invention relates to a bioreactor, in particular a single-use bioreactor, for the culturing of microorganisms or of animal or plant cells by use of a composite element that is attached to a wall of the bioreactor as a connector fitting, as described above, such as, for example, by polymer-to-polymer welding.

The composite element as a connector fitting, is attached—for example, welded—to the bioreactor, in particular the single-use bioreactor, in particular in a permanently fixed manner. The composite element or the connector fitting can, in particular, have the features described above.

In particular, the composite element has an outer frame that is made with or from a polymeric material, whereby the outer frame is attached to the wall of the bioreactor and, in particular, is joined to it in a sterilely tight manner and/or in a hermetically tight manner. Furthermore, the composite element has an inner component that is made with or from a transparent material, such as, for example, glass, or glass ceramic, whereby the inner component is fitted in the outer frame in a sterilely tight manner and/or in a hermetically tight manner, in particular in a permanently fixed manner, and forms a window in the bioreactor, in particular in order to enable a spectral process control from outside of the bioreactor.

The outer frame is preferably tubular in design with a first end and a second end of the tube and is joined to the wall of the bioreactor by being attached, for example, by the first end of the tube to the wall of the bioreactor. Furthermore, the outer frame preferably has a flange and is attached by the flange to the wall of the bioreactor, whereby the flange is preferably arranged between the first end and the second end of the tube or is arranged at the first end of the tube.

The bioreactor, which is designed, in particular, as a single-use bioreactor and, in particular, is designed for receiving fluid media that contain biological material, preferably comprises a plastic, in particular a sterilizable plastic, or is composed of a plastic, in particular a sterilizable plastic.

The bioreactor can preferably be autoclaved together with the composite element that is attached to it.

Finally, the invention also relates to a method for the propagation or culturing of biological material, in particular of microorganisms or cells in a bioreactor, in particular in a single-use bioreactor, as described above, for example, having a biocompatible composite element that is attached to a wall of the bioreactor as a connector fitting, in particular as described above wherein a spectral process control occurs from outside of the bioreactor through the window that is formed and wherein, in particular, a physical, chemical, or biological measured variable is recorded from outside the bioreactor through the window that is formed.

A preferred method for the propagation or culturing of biological material comprises the introduction of liquid, particularly biological material or a precursor of biological material, into a bioreactor, such as that described here, as well as the recording of a physical, chemical, or biological measured variable by use of a window formed by a connector fitting as described above.

Advantageously, the methods described here for propagation or culturing can comprise the production of pharmaceuticals, in particular biopharmaceuticals.

Preferably, the bioreactor is sterilized after attachment, in particular inseparable attachment, of the connector fitting or is autoclaved. Measured values can then be recorded from outside of the bioreactor. Preferably, a spatially resolved measurement can be conducted, in order to record, for example, metabolic processes in a spatially resolved manner.

The method for the propagation or culturing of biological material can comprise the measurement, from outside of the bioreactor, of the radiation intensity and/or the wavelength of the electromagnetic radiation in the interior of the bioreactor, in particular in a spatially resolved manner.

When, for a defined period of time, electromagnetic radiation of defined wavelength, preferably 250 nm, is irradiated from outside of the bioreactor into the bioreactor and, following this irradiation, measurement is performed inside of the reactor in a broad-band or selective manner at a given wavelength, in particular at 270 nm, and a radiation intensity and/or a wavelength of the electromagnetic radiation in the interior of the bioreactor is measured, it is possible in this way to detect fluorescently emitted portions of the light and to analyze them with respect to defined metabolic processes within the photobioreactor.

In accordance therewith, it can be provided, for example, that, from outside of the bioreactor for a defined period of time, electromagnetic radiation of a defined wavelength, preferably 250 nm, is irradiated into the bioreactor and, after this irradiation, a radiation intensity and/or wavelength of the electromagnetic radiation in the interior of the reactor is or are measured from the outside after broadband or selective irradiation at a wavelength of, in particular, 270 nm.

In the method disclosed here, phototropic or mixotropic microorganisms that have been altered by mutagenesis, in particular also microalgae, yeast, and bacteria, can be used.

BRIEF DESCRIPTION OF THE DRAWINGS

In the following, a number of special exemplary embodiments of the invention, which are not to be understood as conclusive, in particular glass-to-polymer seals (GTPS), are explained with reference to the appended drawings. Shown are:

FIGS. 16 and 17 perspective views of a composite element mounted on a bioreactor in accordance with the first embodiment;

FIG. 18 a sectional view of a composite element mounted on a bioreactor in accordance with the first embodiment.

DETAILED DESCRIPTION

Figure 1:
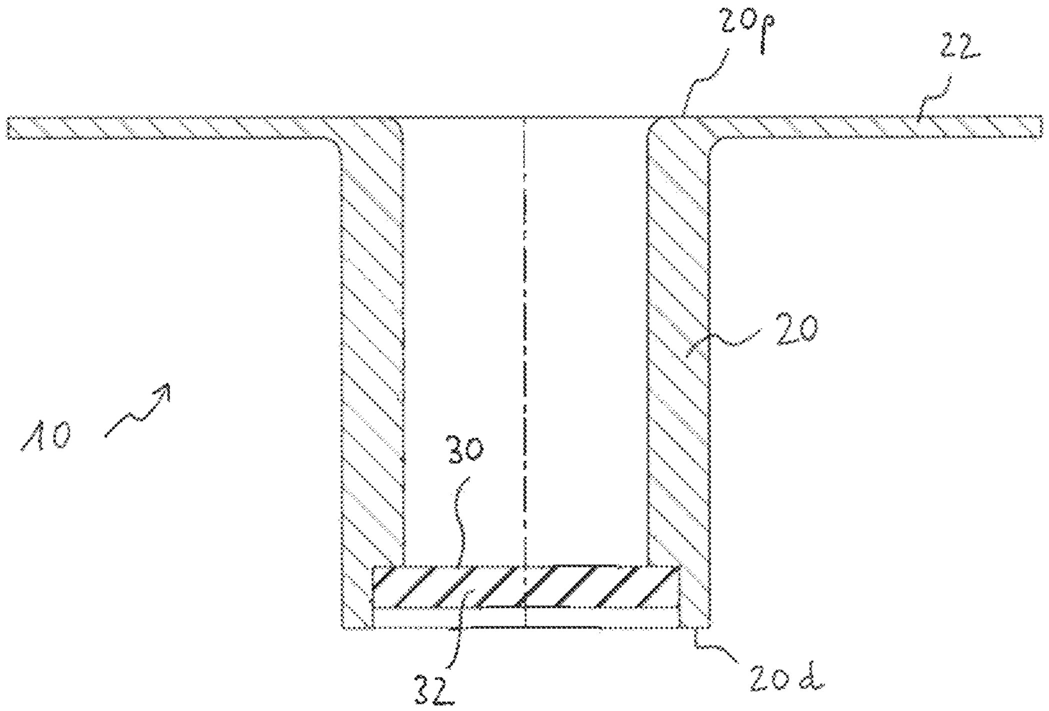
FIG. 1 a sectional view of a composite element in accordance with a first embodiment.
Figure 19:
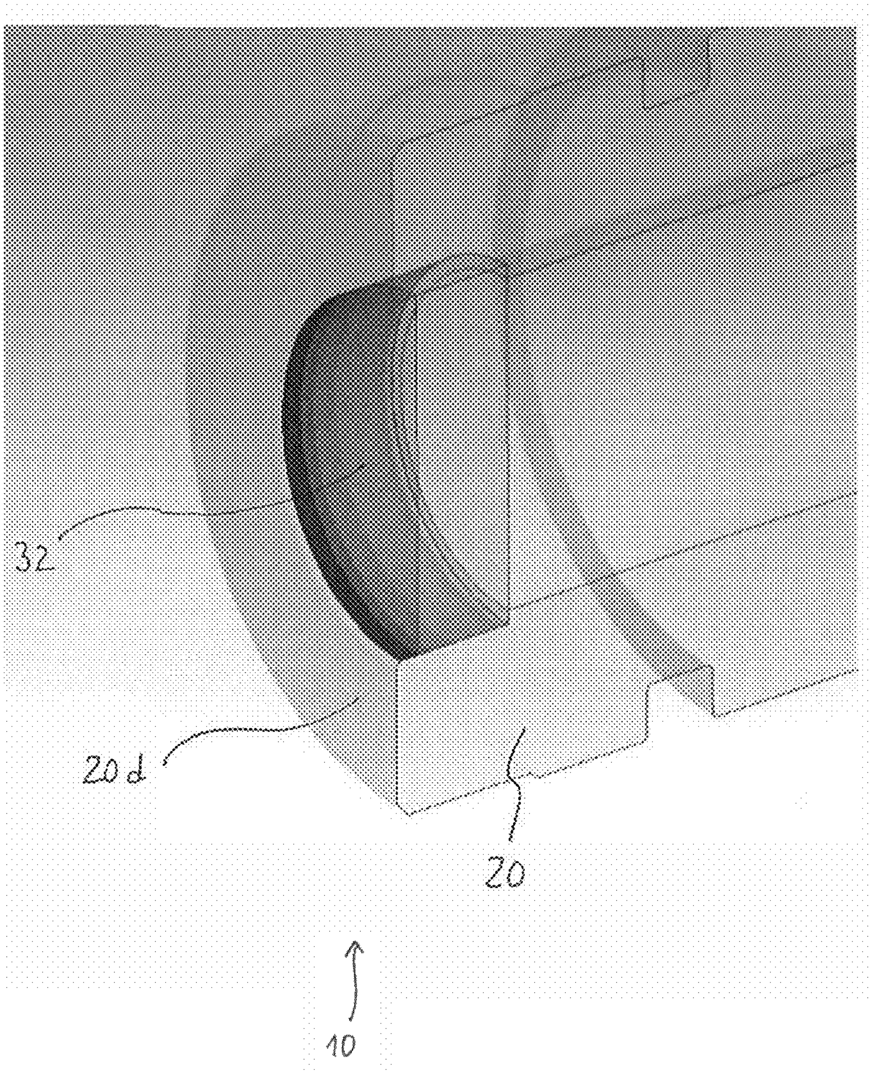
FIG. 19 a perspective detail view of a composite element in accordance with the first embodiment.

The composite element (10) shown in FIG. 1 and FIG. 19 comprises an outer frame (20), which is made of a polymer, such as, for example, polyether ether ketone (PEEK), and an inner component (30), which is designed as a one-piece transparent structural part (32) made of transparent material, such as, for example, glass.

In this embodiment, what is involved is a pressure polymerization incorporation, which, for example, can be carried out as follows: The transparent structural part (32), in particular glass, is inserted under compressive stress in the polymer outer frame (20).

For this purpose, the outer frame (20), which is designed as a polymer molding, is heated (for example, PEEK to 200° C.), the transparent structural part (32), which, in this example, is designed as a disc, is inserted with a greater diameter than the inner diameter of the port and then cooled. This results in an autoclavable and sterilely tight pressure polymerization incorporation.

Figure 5:
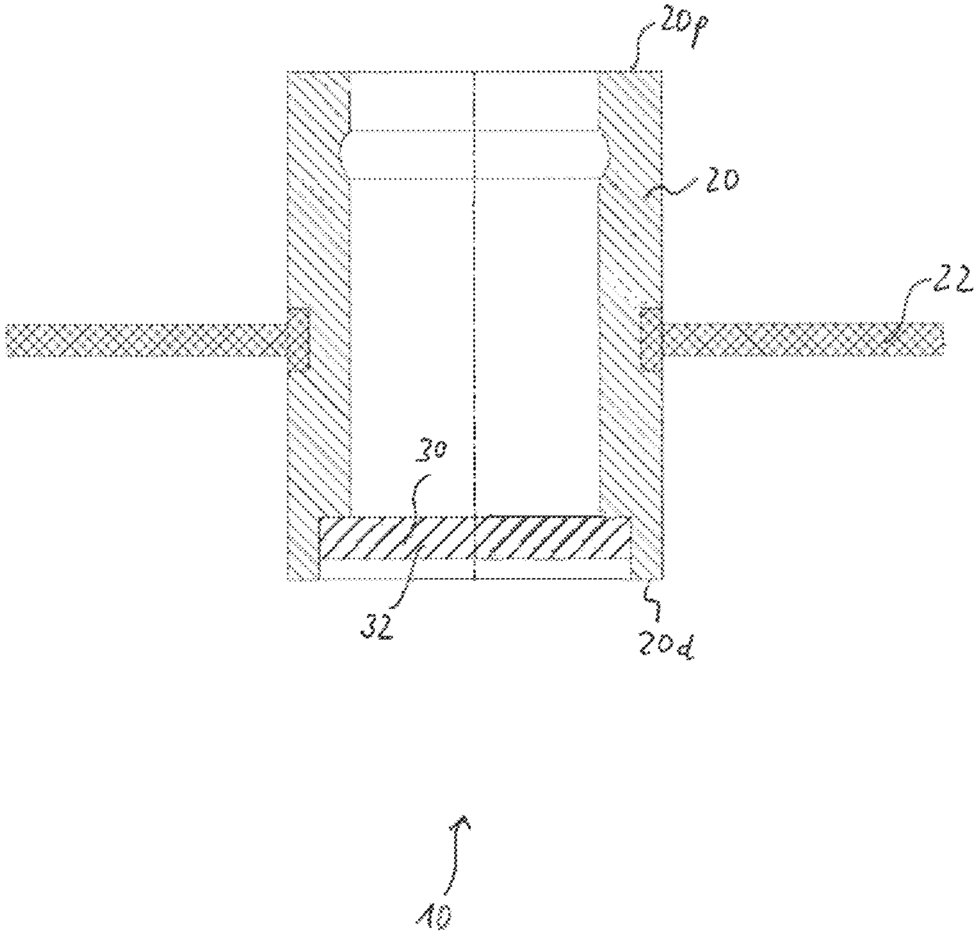
FIG. 5 a sectional view of a composite element in accordance with a fifth embodiment.

The polymer outer frame (20) has a flange (22), with the flange (22) being arranged at the first (proximal) end of the tube (20*p*). However, a flange (22) can also be provided at another point, in particular between the first end of the tube (20*p*) and the second end of the tube (20*d*), as illustrated in FIG. 5.

Figure 2:
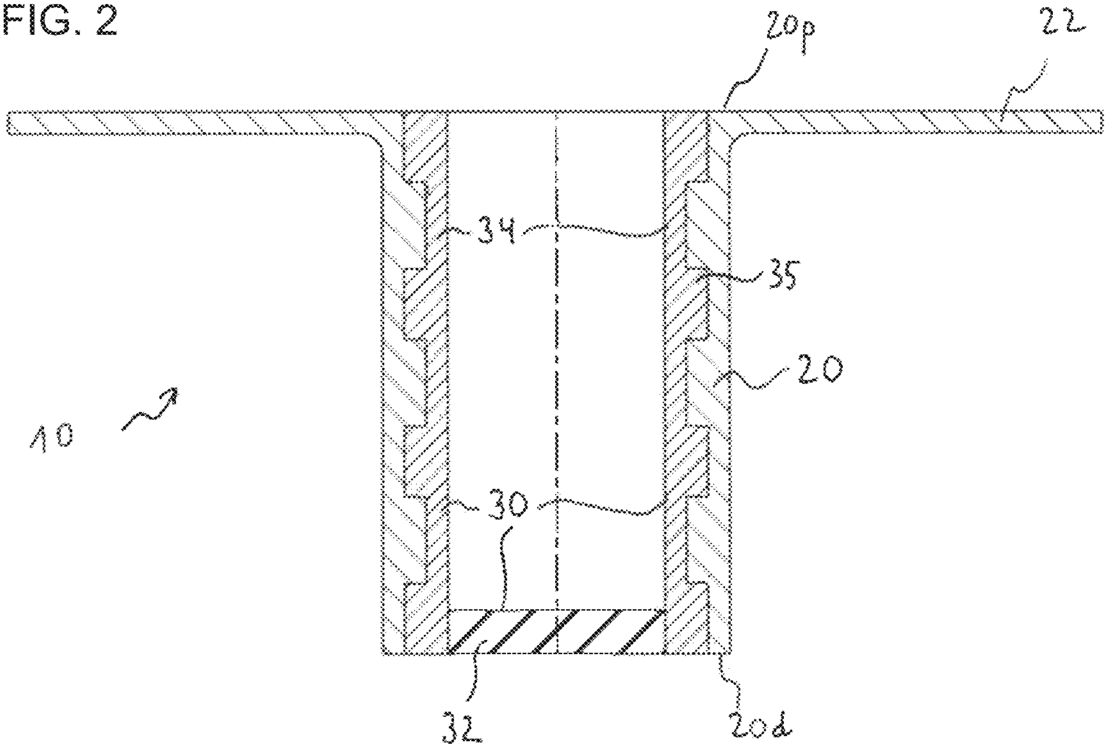
FIG. 2 a sectional view of a composite element in accordance with a second embodiment.

The composite element (10) shown in FIG. 2 comprises an outer frame (20) made from a polymer, such as, for example, polyethylene (PE), and a two-part inner component (30) that has a disc-shaped transparent structural part (32) made of glass, for example, and a tubular connecting part (34), made of metal, for instance, such as, for example, 1.4404 stainless steel. In this example, the connecting part (34) surrounds the transparent structural part (32).

In this embodiment, what is involved is a glass/metal/polymer composite, which can be produced, for example, as follows: The pressure sealing of the transparent structural part (32) is conducted in a sterilely tight manner and/or in a hermetically tight manner in the connecting part (34), which, in this example, is designed as a profiled hollow metal cylinder. The connecting part (34) or the thus formed inner component (30) is coated in a sterilely tight manner with a polymer, such as, for example, polyethylene (PE), polypropylene (PP), polyamide (PA), polyethylene terephthalate (PET), ethylene vinyl alcohol (EVOH), polyether ether ketone (PEEK), polyaryl ether ketone (PAEK), polysulfone (PSU), polyphenylene sulfide (PPS), or a multimaterial molding containing a number of polymers, to create the desired dimension of the structural part, inclusive of a flange (22). Accordingly, the outer frame (20) can comprise one or a plurality of the previously mentioned materials or be composed thereof or be produced or be producible from them.

The polymer outer frame (20) has a flange (22) at the first end of the tube (20*p*). Alternatively, however, a flange (22) can also be provided at another point, in particular between the first end of the tube (20*p*) and the second end of the tube (20*d*), as illustrated in FIG. 6 and FIG. 7.

Figure 6:
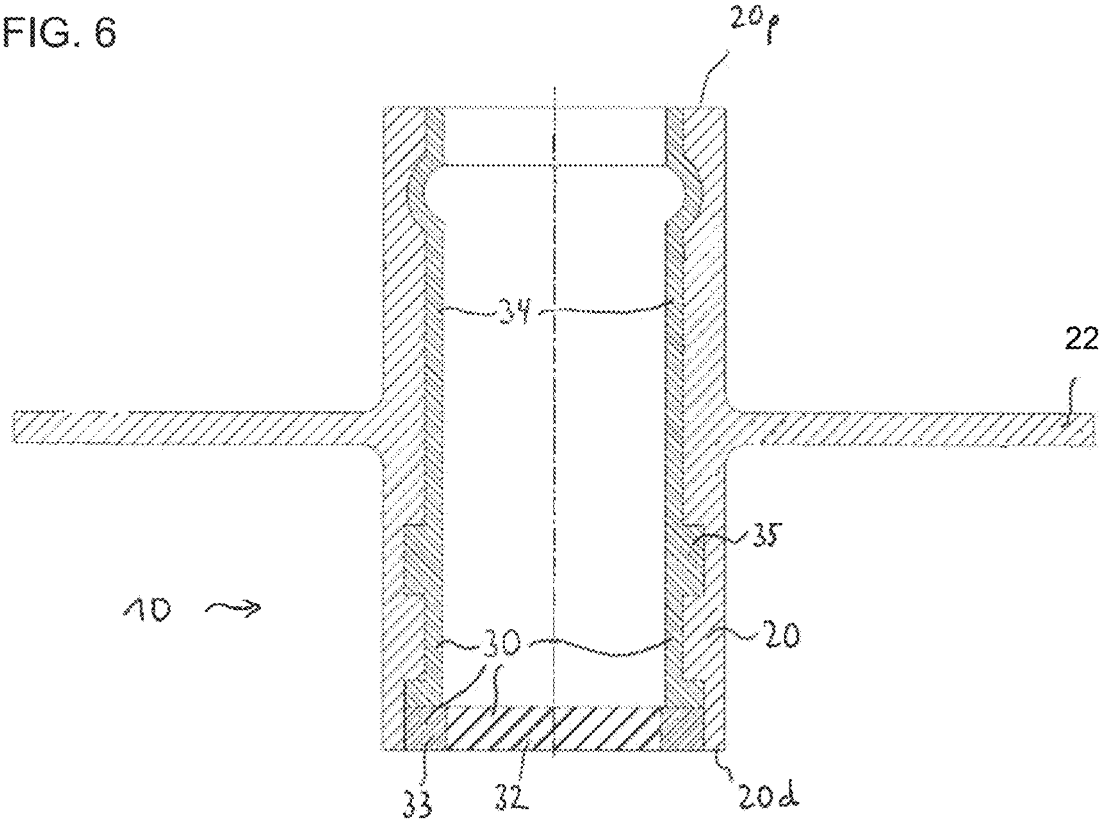
FIGS. 6 and 7 sectional views of composite elements in accordance with a seventh embodiment.
Figure 7:
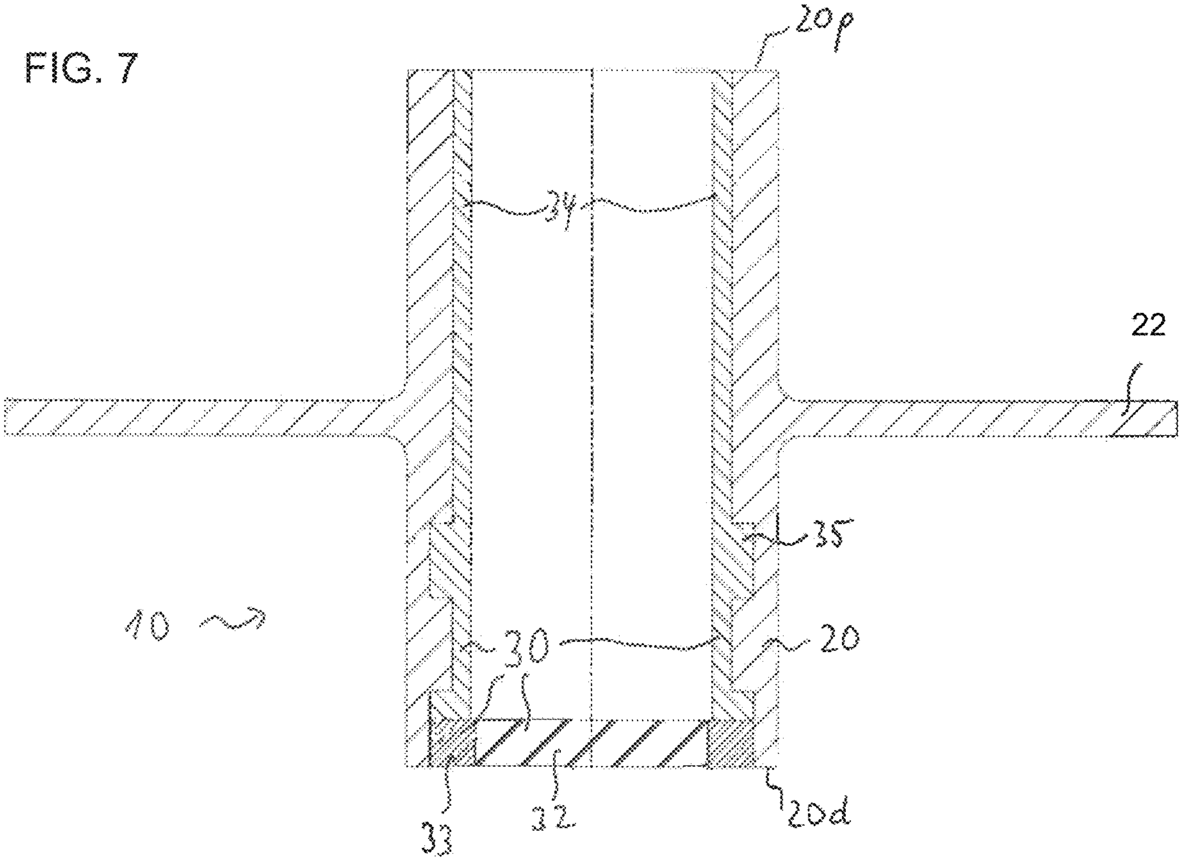

The composite elements shown in FIG. 6 and FIG. 7 have, in addition, a multipart (here: three-part) inner component (30), with the connecting part (34) being joined both directly to the outer frame (20) and indirectly to the transparent structural part (32). At its front end, the connecting part (34) is joined to a frame (33) that surrounds the transparent structural part (32) in such a way that the transparent structural part (32) is fitted in the frame (33) in a sterilely tight manner, preferably in a hermetically tight manner; the frame (33), in turn, is joined to the connecting part (34) in a sterilely tight manner, preferably in a hermetically tight manner; and the connecting part (34), in turn, is fitted in the outer frame (20) in a sterilely tight manner, preferably in a hermetically tight manner.

Figure 3:
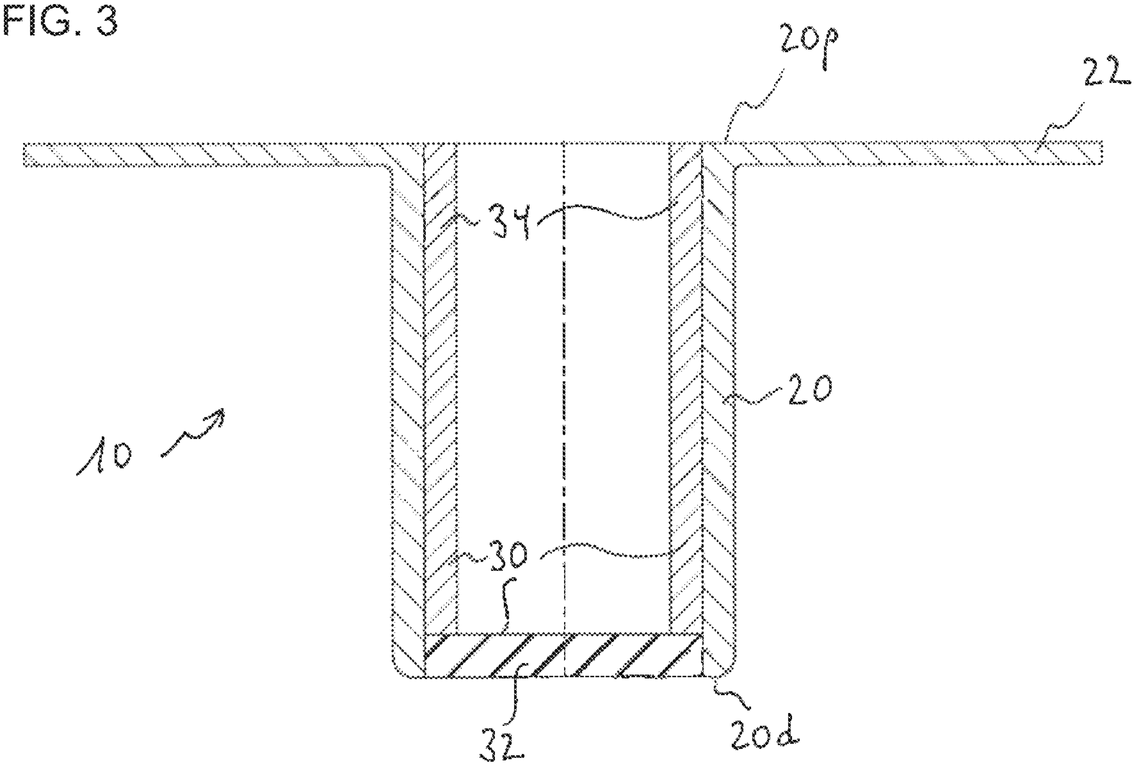
FIG. 3 a sectional view of a composite element in accordance with a third embodiment.

The composite element (10) shown in FIG. 3 comprises, in turn, a polymer outer frame (20) and a two-part inner component (30) having a transparent structural part (32) and a tubular connecting part (34), whereby, in this example, the connecting part (34) is designed as a hollow cylinder made of a transparent material, especially glass. Furthermore, in this case, the connecting part (34) abuts, at its front end, the transparent structural part (32).

In this embodiment, what is involved is a glass/glass/polymer composite, which, for example, can be produced as follows: The connecting part (34), which, in particular, is designed as a glass cylinder, is ground and polished at its front end; in addition, the transparent structural part (32), which is designed, for example, as a disc, is ground and polished and, namely, these connecting parts are ground and polished such that coherent surface areas are created.

Afterwards, the two parts are joined such that they adhere to each other through intermolecular forces (that is, the disc is pushed onto the glass cylinder). Subsequently, the two parts can be joined in a fixed manner by laser welding, for example, in order to produce in this way a permanently sterilely tight connection. The inner component (30) thus formed is, in turn, coated with a polymer, such as, for example, polyethylene (PE), in a sterilely tight manner to create the desired dimension of the structural part, inclusive of a flange (22).

The coating results in formation of the polymer outer frame (20), which, in this example, has a flange (22) at the first (proximal) end of the tube (20*p*). However, a flange (22) can also be formed at another point, in particular between the first end of the tube (20*p*) and the second end of the tube (20*d*), as illustrated in FIG. 8.

Figure 8:
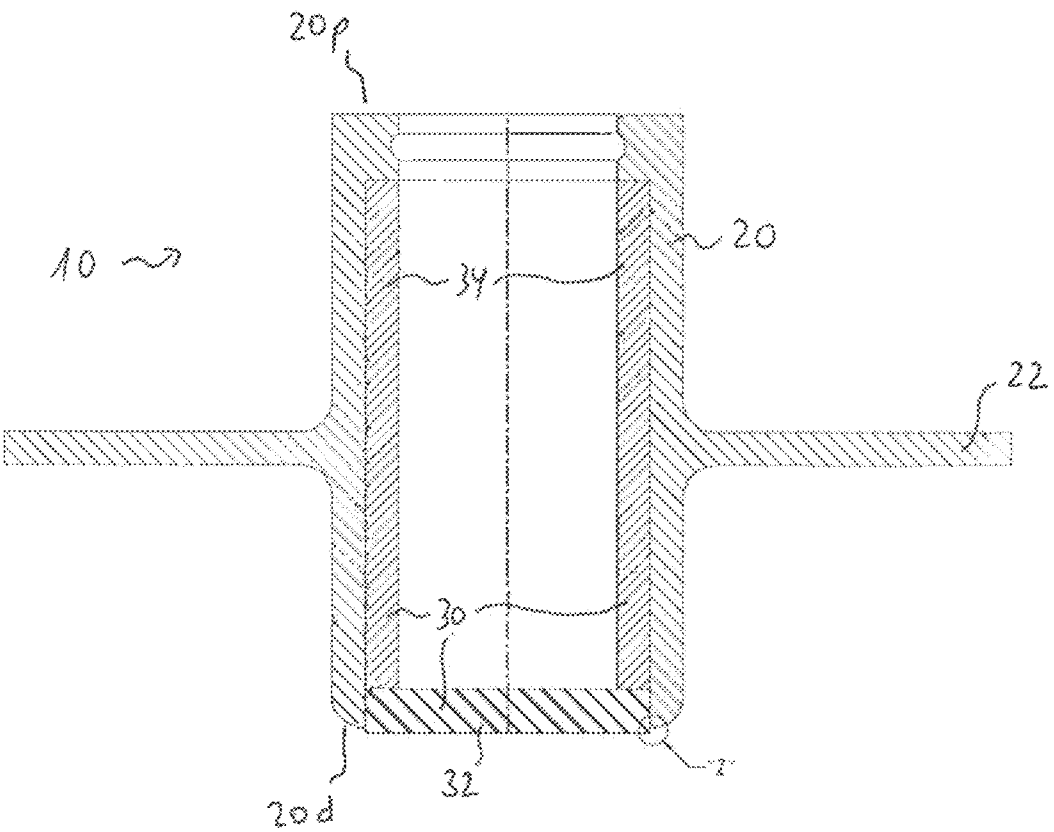
FIGS. 8 and 9 a sectional view and a detail view of a composite element in accordance with a sixth embodiment.
Figure 9:
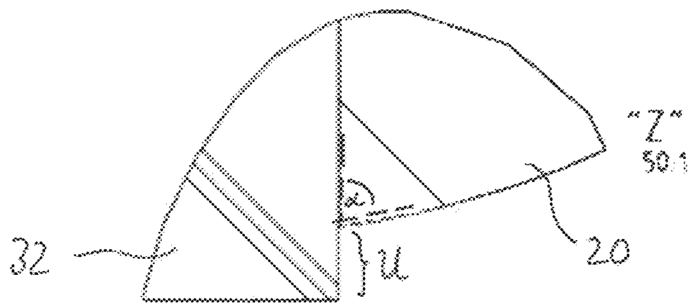

Beyond this, FIG. 9 shows a detail view of the connecting element (10) shown in FIG. 8. The transparent structural part (32) here projects out of the outer frame (20), so that an overhang U is formed. Because the wetting angle of contact of the material of the outer frame on the material of the transparent structural part (20) is less than 90°, an angle α of less than 90° is correspondingly formed between the outer frame (20) and the transparent structural part (32).

Figure 4:
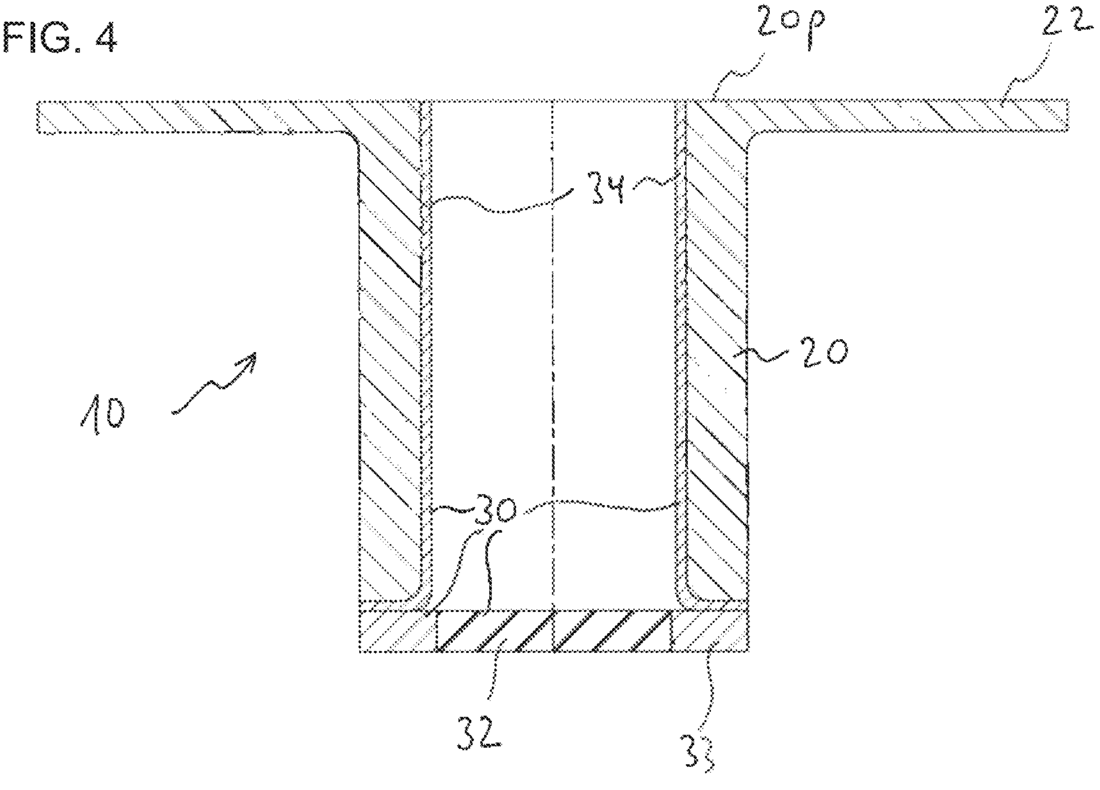
FIG. 4 a sectional view of a composite element in accordance with a fourth embodiment.

The composite element (10) shown in FIG. 4 comprises a polymer outer frame (20) and a multipart component (30) having a transparent structural part (32), a frame (33) that surrounds the transparent structural part (32), and a tubular connecting part (34). At its front end, the connecting part (34) is joined to the frame (33) that surrounds the transparent structural part (32) in such a way that the transparent structural part (32) is fitted in the frame (33) in a sterilely tight manner, preferably in a hermetically tight manner; the frame (33), in turn, is joined to the connecting part (34) in a sterilely tight manner, preferably in a hermetically tight manner; and the connecting part (34), in turn, is fitted in the outer frame (20) in a sterilely tight manner, preferably in a hermetically tight manner.

In this example, the inner component (30) projects at least partially out of the outer frame (20), in particular by the transparent structural part (32) and the frame (33). Alternatively, however, it can also be provided that the outer frame (20) completely surrounds the inner component (30) along its length.

In this example, the outer frame (20) has, in turn, a flange (22) at the first end of the tube (20*p*). However, a flange (22) can also be provided at another point, in particular between the first end of the tube (20*p*) and the second end of the tube (20*d*), as illustrated in FIG. 10 and FIG. 12.

Figure 10:
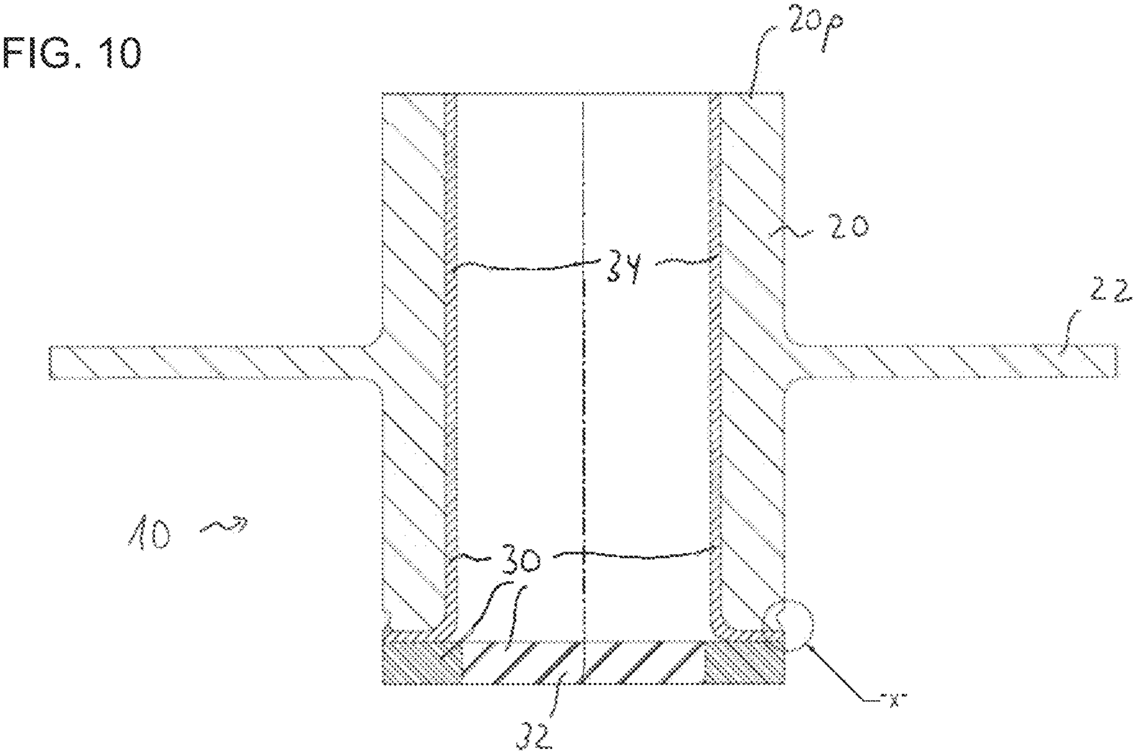
FIGS. 10 and 11 a sectional view and a detail view of a composite element in accordance with an eighth embodiment.
Figure 11:
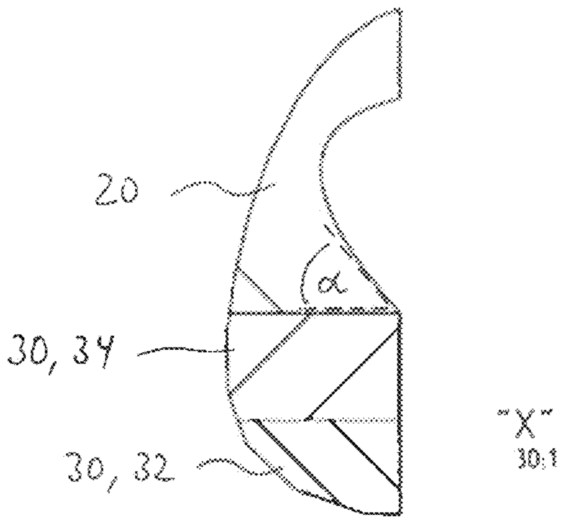
Figure 12:
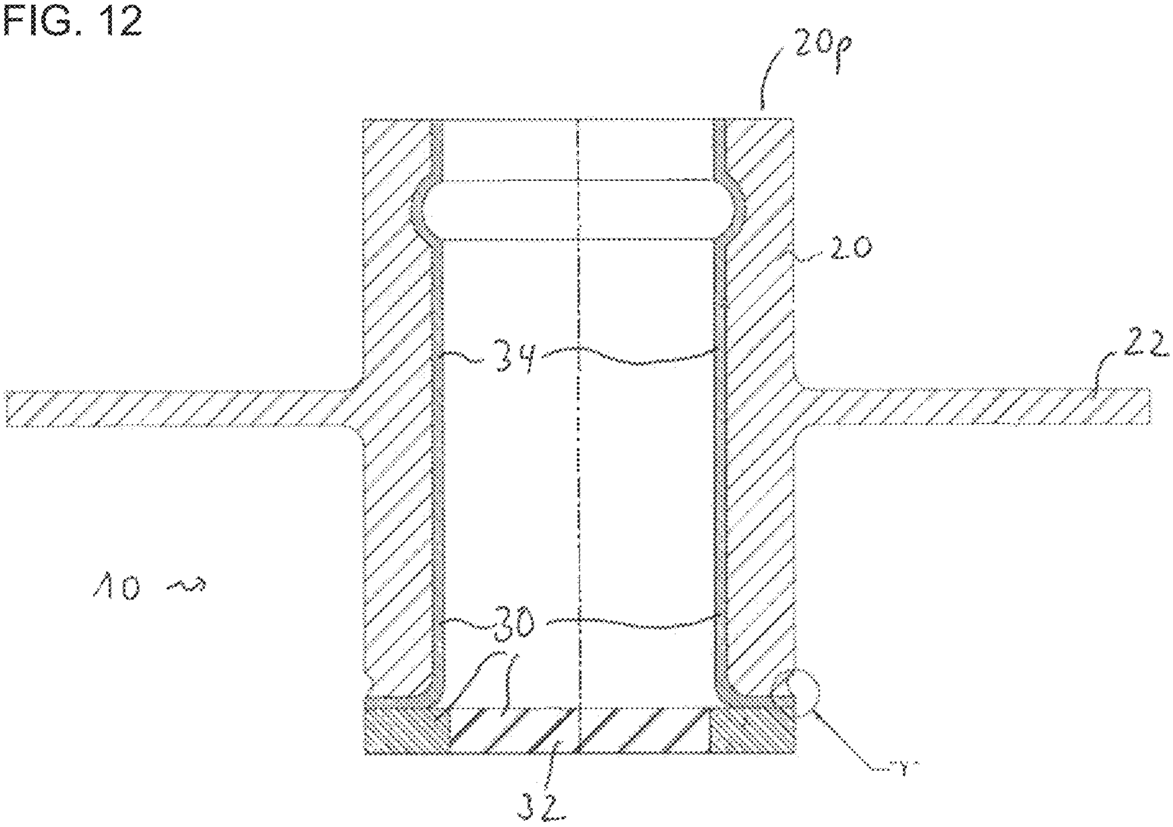
FIGS. 12 and 13 a sectional view and a detail view of a composite element in accordance with a ninth embodiment.
Figure 13:
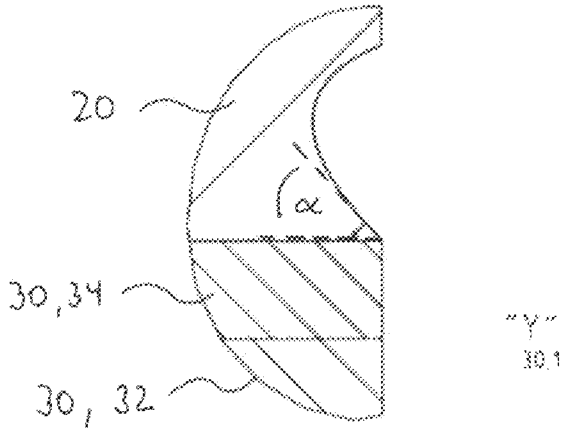

Beyond this, FIG. 11 and FIG. 13 show detail views of the connecting element (10) shown in FIG. 10 and FIG. 12. Between the outer frame (20) and the inner component (30), an angle α of less than 90° is provided. For this purpose, an arched-shape recess (23) is introduced in the outer frame (20). This recess (23) is found in the polymeric material at the material transition to the inner component (30).

Figure 14:
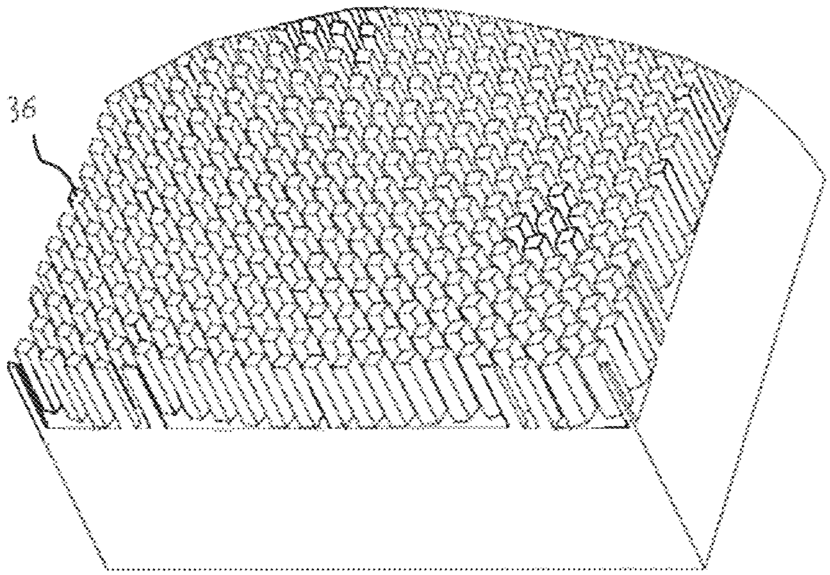
FIGS. 14 and 15 a perspective view and a view from the top of a surface of a connecting part having a microstructure.
Figure 15:
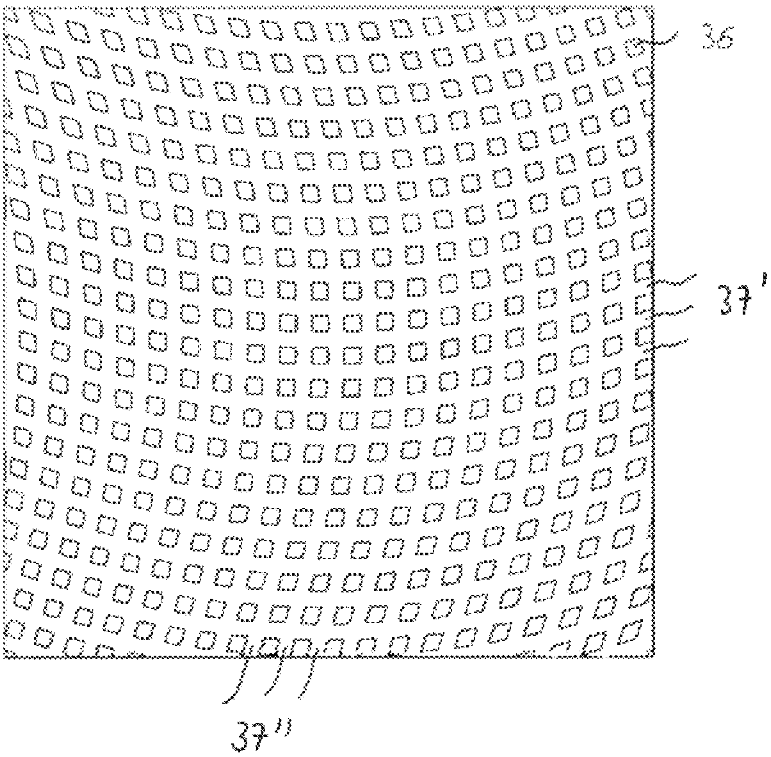

FIGS. 14 and 15 show a surface of a connecting part in which a microstructure in the form of numerous projections (36) is introduced. The majority of projections (36) between the grooves are formed by way of a bunch of grooves (37') that is crossed by a second bunch of grooves (37").

FIGS. 16, 17, and 18 show a bioreactor wall (40) as a part of a bioreactor with a through passage (42), also referred to as a port (42), situated in it, which forms an opening into the interior of the bioreactor, whereby a composite element (10) extends at least partially into the opening formed by the through passage (42). In this example, the composite element (10) is designed in accordance with the composite element (10) shown in FIG. 1. Obviously, however, any previously described composite element (10) can extend through the through passage (42) illustrated here.

Installed in the interior of the composite element (10) is a measuring probe (50), which makes it possible to carry out measurements in the interior of the bioreactor, whereby the measurement is produced through the transparent structural part (32) of the composite element (10). By means of a sealing element (44), such as, for example, an O-ring, the composite element (10) is preferably fluidtight and is held most preferably in a sterilely tight manner and/or in a hermetically tight manner with respect to the through passage (42) of the bioreactor wall (40), in particular in a form-fitting and friction-fitting manner. The measuring probe (50) engages, in turn, by means of a friction element (46), preferably an O-ring, in a friction-fitting connection with the composite element (10), whereby the friction element (46) is held in a cylindrical recess of the composite element by way of a compression element (compression ring) (48), which, in particular, is essentially annular in shape and which exerts a definably adjustable force on the friction element (46) in the axial direction of the composite element (10).

By means of a union nut (52), which is formed, in particular, as a cap nut, the composite element (10) can be detached, but held in fixed position at the through passage (42) of the bioreactor wall (40). By means of a retaining ring or snap ring (54), the union nut (52) is held in a rotatable manner, although with only slight axial play, at the composite element (10).

What is claimed is:

1. A biocompatible composite element for a bioreactor, comprising:
- an outer frame comprising a polymeric material, the outer frame being configured for inseparable attachment to a wall of the bioreactor; and
- an inner component comprising a transparent material selected from a group consisting of glass, sapphire, and glass ceramic,
- wherein the inner component is secured in the outer frame in an inseparable hermetically tight manner,
- wherein the inner component is configured for a spectral process control through the transparent material of the inner component, and
- wherein the transparent material is in direct contact with and is under a compressive stress in the outer frame, the compressive stress being at least 50 MPa.

2. The biocompatible composite element of claim 1, wherein the transparent material exhibits a transmittance that is selected from a group consisting of: greater than 75% in a spectral range with a wavelength of 190 to 5500 nm; greater than 90% in a spectral range with a wavelength of 190 to 5500 nm; greater than 75% in a spectral range with a wavelength of 190 to 2800 nm; greater than 80% in a spectral range with a wavelength of 190 to 2800 nm; greater than 90% in a spectral range with a wavelength of 190 to 2800 nm; greater than 75% in a spectral range with a wavelength of 190 to 2700 nm; greater than 90% in a spectral range with a wavelength of 190 to 2700 nm; and any combinations thereof.

3. The biocompatible composite element of claim 1, wherein the outer frame has a structure selected from a group consisting of: an annular cross section so that the outer frame surrounds the inner component; a tubular having a first end and a second end with the first end being configured for inseparable attachment to the wall of the bioreactor; a flange being configured for inseparable attachment to the wall of the bioreactor; an outer thread configured for inseparable attachment to the wall of the bioreactor; and any combinations thereof.

4. The biocompatible composite element of claim 1, wherein the inner component is a single component having a plate or disc-shape.

5. The biocompatible composite element of claim 1, wherein the inner component is fitted vertically under compressive stress in the outer frame.

6. The biocompatible composite element of claim 1, wherein the outer frame comprises a material selected from a group consisting of polyether ether ketone (PEEK), polyethylene (PE), and a material having a wetting angle of contact that is less than 90° with a material of the inner component.

7. The biocompatible composite element of claim 1, wherein the compressive stress is more than 75 MPa.

8. The biocompatible composite element of claim 1, wherein the compressive stress is more than 100 MPa.

9. A biocompatible composite element for a bioreactor, comprising:

an outer frame comprising a polymeric material, the outer frame being configured for inseparable attachment to a wall of the bioreactor; and an inner component that comprises a transparent structural part and a tubular connecting part, wherein the transparent structural part comprises a transparent material selected from a group consisting of glass, sapphire, and glass ceramic, wherein the tubular connecting part is directly joined both to the transparent structural part and to the outer frame, and wherein the transparent material is under a compressive stress of at least 50 MPa.

10. The biocompatible composite element of claim 9, wherein the tubular connecting part comprises a plurality of projections that increase a contact surface area with the outer frame.

11. The biocompatible composite element of claim 9, wherein the transparent structural part is arranged at a second end of the tubular connecting part.

12. The biocompatible composite element of claim 9, wherein the tubular connecting part surrounds the transparent structural part in such a way that the transparent structural part is fitted in the tubular connecting part in a hermetically tight manner.

13. The biocompatible composite element of claim 9, wherein the tubular connecting part is made from a material selected from a group consisting of metal, stainless steel, and austenitic-ferritic duplex steel.

14. The biocompatible composite element of claim 9, wherein the tubular connecting part and transparent structural part are each fitted in the outer frame.

15. The biocompatible composite element of claim 9, wherein the tubular connecting part is made from a common transparent material as the transparent structural part.

16. The biocompatible composite element of claim 9, wherein the tubular connecting part is made from a non-transparent material selected from a group consisting of ceramic, metal, oxidizable metal, and aluminum.

17. The biocompatible composite element of claim 16, wherein the tubular connecting part has an oxide layer on a surface that adjoins the transparent structural part.

18. The biocompatible composite element of claim 9, wherein the inner component projects, at least partially, out of the outer frame.

19. The biocompatible composite element of claim 9, wherein the tubular connecting part is laser-welded to the transparent structural part.

* * * * *